(12) United States Patent
Ferek-Petric

(10) Patent No.: US 6,574,503 B2
(45) Date of Patent: Jun. 3, 2003

(54) GUI CODING FOR IDENTIFICATION OF DISPLAYABLE DATA QUALITY FROM MEDICAL DEVICES

(75) Inventor: Bozidar Ferek-Petric, Zagreb (HR)

(73) Assignee: Medtronic, Inc., Minneapolis, MN (US)

( * ) Notice: Subject to any disclaimer, the term of this patent is extended or adjusted under 35 U.S.C. 154(b) by 104 days.

(21) Appl. No.: 09/841,261

(22) Filed: Apr. 24, 2001

(65) Prior Publication Data

US 2002/0068962 A1 Jun. 6, 2002

Related U.S. Application Data

(60) Provisional application No. 60/199,769, filed on Apr. 26, 2000.

(51) Int. Cl.[7] .............................................. A61B 5/044
(52) U.S. Cl. ........................... 600/523; 607/32; 607/60; 600/509
(58) Field of Search .................................. 600/508, 509, 600/522, 523; 607/30, 32, 59, 60

(56) References Cited

U.S. PATENT DOCUMENTS

| | | | |
|---|---|---|---|
| 4,556,063 A | 12/1985 | Thompson et al. | 128/419 PT |
| 5,127,404 A | 7/1992 | Wyborny et al. | 128/419 P |
| 5,342,408 A | 8/1994 | deCoriolis et al. | 607/32 |
| 5,345,362 A | 9/1994 | Winkler | 361/681 |
| 5,745,479 A | 4/1998 | Burns et al. | 370/245 |
| 5,752,976 A | 5/1998 | Duffin et al. | 607/32 |
| 5,941,829 A * | 8/1999 | Saltzstein et al. | 600/509 |
| 6,259,944 B1 * | 7/2001 | Margulis et al. | 600/509 |
| 6,325,756 B1 * | 12/2001 | Webb et al. | 600/300 |
| 6,406,426 B1 * | 6/2002 | Reuss et al. | 600/300 |
| 6,418,346 B1 * | 7/2002 | Nelson et al. | 607/59 |

FOREIGN PATENT DOCUMENTS

WO    0103575 A1    1/2001    ............ A61B/5/00

* cited by examiner

Primary Examiner—Carl Layno
(74) Attorney, Agent, or Firm—Girma Wolde-Michael

(57) ABSTRACT

Disruptions and corruptions in displayable data are identified using various color codes and marker schemes. Specifically, clinical data communicated across one or more network connections is continuously monitored and evaluated for disruptions, continuity, integrity and accuracy. A color coding or similar method for highlighting and characterizing discontinuities are used to mark data or communication elements and displays that are suspect of channel disruption, corruption and other discrepancies.

18 Claims, 4 Drawing Sheets

GUI CODING FOR IDENTIFICATION OF DISPLAYABLE DATA QUALITY FROM MEDICAL DEVICES

This application claims the benefit of provisional application No. 60/199,769 filed on Apr. 26, 2000.

FIELD OF THE INVENTION

The present invention generally relates to implanted medical devices (IMDs) and instruments. Specifically, the invention relates to a graphic user interface (GUI) in which disruptions in the displayable ECG data stream are highlighted using color-coded schemes to indicate communication channel disruption and problems with displayable data quality, collected from medical devices. More specifically, the invention is compatible with and adaptable to a network in which various medical devices communicate and exchange clinical data across various network systems.

BACKGROUND OF THE INVENTION

IMDs are implanted to treat and/or monitor a variety of patients who have a variety of individual or multiple medical conditions. Such IMDs may include, without limitation, drug pumps, nerve stimulators, cardiac defibrillators, and cardiac pacemakers. Once implanted, many of these IMDs require the downloading of data, collected and stored by the IMD, to a medical instrument, usually a programmer. Based on these data, the IMD may be reprogrammed and/or reinterrogated to ensure operational parameters that are appropriate to the patient.

Programmers are instruments that downlink to the IMD as well as receive an uplink from the IMD. These programmers use customized software that can be characterized as a windowing environment with overlapping windows and a GUI using multiple colors. The windowing environment makes the customized software familiar to the user. One of the important aspects of a GUI is its use of color or other forms of distinctive notice to highlight and call the user's attention to certain portions of the screen or to clarify and segment specific pieces of information.

Electrocardiogram (ECG) and/or intracardiac electrogram (EGM) signals are often the only few continuous data stream of graphic information presented on a programmer screen. The ECG tracing is essentially nothing more than a continuous time-dependent graph of the QRST complex as seen by external leads attached to the skin. The EGM, on the other hand, is a representation of the same complex as seen by the implanted lead(s). ECGs are used to monitor the patient's cardiac conduction system as well as the delivery of the therapy specific to the IMD. When a programmer of the type disclosed in U.S. Pat. No. 5,345,362 issued to Winkler, et al., incorporated herein in its totality, is used, a physician may select various colors on the programmer screen to differentiate one cardiac vector from another, as well as segmenting the ECG from the intracardiac EGM.

Typically, a programmer used during a telemetry procedure is positioned remotely from the patient. The programming head of the programmer, containing at least an antenna, is connected to the body of the programmer via a stretchable coil cable. The programming head is positioned over the patient's implanted device site for programming or interrogating the implanted device. The programmer typically consists of one or more microprocessors and contains a programmable memory capable of storing executable programs under the control of the operator via a user interface, e.g., the programmer's screen. The IMD may receive command instructions from the programmer. Such command instructions are referred to as downlink transmissions, i.e., transmissions from the external device or programmer to the IMD. Typically, the downlink transmissions may include program instructions or steps for directing the operation of the IMD.

The downlink instructions may also request a data dump of programmed parameters and diagnostic data. Such transmissions are typically referred to as uplink transmissions, i.e., transmissions from the implantable medical device to the external device. In other words, in addition to transmitting commands, the programmer may receive and transmit data from the IMD. At times, communication between the IMD and the external instrument may be limited to transmissions by only one of the devices with the other device receiving those transmissions. Alternatively, communication between the IMD and the external instrument may include transmissions to and by both devices.

The communication between the IMD and the external instrument, e.g., programmer, is facilitated by receiving and transmitting circuitry included within the implanted medical device and the external device. The implanted medical device includes a receiver and transmitter circuitry that may cooperate with other circuitry of the IMD to receive commands from and transmit data to the external instrument. Further, the external instrument includes transmitting and receiving circuitry for communicating with the implanted medical device. Both the IMD and the external instrument include antenna structures coupled to the receiver and transmitter circuitry for transmitting and receiving RF/telemetry signals.

Various systems for performing telemetry with regard to implanted devices are known. For example, such systems are described in U.S. Pat. No. 5,127,404 issued to Wyborny, et al.; U.S. Pat. No. 4,556,063 issued to Thompson, et al.; U.S. Pat. No. 5,342,408 issued to de Coriolis et al.; and U.S. Pat. No. 5,752,976 issued to Duffin, et al.: International Application, WO 01/03575 A1, System for Remote Communication with an Implantable Medical Device by Ferek-Petric, all incorporated herein by reference in their entirety.

Errors may occur in all communication systems. A variety of techniques have been developed to detect such errors and, when possible, correct them. For example, in a standard local area network, such as Ethernet, error detection mechanisms, such as cyclic redundancy codes (CRC) are implemented at various levels of protocol.

In wireless local area networks, the bit error rate of a transmission is affected by a number of factors not present in a classic wired LAN. Thus, the bit error rate of a given transmission depends on the amount of power transmitted, the process by which the receiver receives that power, the presence of noise and/or interference, and the quality of the transmission once it reaches the receiver. In addition, there are a number of sources of interference that may be encountered in such systems. For example, for systems transmitting in the industrial, scientific and medical (ISM) band, around 2.4 GHz, as regulated by the Federal Communications Commissions (FCC) Part 15 Regulations, interference may arise from other sources within the same band, such as microwave ovens, security systems and car alarms. Also, additive white gaussian noise, thermally generated naturally, may be a source of interference. Further, these types of interference may occur even after a user has been allocated a channel for communicating. Thus, a data packet may be corrupted early or late in a transmission sequence. Relying on the standard CRC techniques in local area network packets alone may be insufficient in these environments. For instance, CRC can detect burst errors up to the length of CRC itself. In wireless environments, burst errors can be significant portions of packet length, entire packets, or multiple packets.

Patients with IMDs require periodic monitoring, which can be within a clinic or hospital setting, or from a remote setting, e.g., from a patient's home. Within the clinic or hospital setting, a physician or clinician is typically present and interacts with the programmer directly. Any interruption in the data stream can be quickly identified and addressed by qualified medical personnel under most circumstances. For example, a short interruption in the ECG tracing should be apparent, unless the physician/clinician's attention to the programmer screen is also interrupted. However, even if the user's attention has not wavered, a pause in the ECG tracing might easily be confused with a physiologic cause, inter alia, sinus pause or sinus arrest. But, due to the close attendance of a qualified medical technician, the situation can be quickly diagnosed and any corrective action, if necessary, be taken. Still, it would be advantageous to have a system by which medical personnel can quickly differentiate between pauses on the ECG tracing due to a mechanical, electrical, telemetric disruption and one due to a physiologic condition in the heart.

The situation may be entirely different when monitoring takes place from a remote environment via wireless technology. Patients live in various locations, including remote places, such as islands, mountainous areas, or places where travels may be difficult at all times or at only specific times of the year. Moreover, regardless of where the patient may live, the attending physician may, at times, desire additional input from the IMD for subsequent programming. Thus, rather than have the patient travel to the clinic, he may request a remote monitoring session. During any remote monitoring session, it can be very difficult for the technician to determine whether any interruption in the ECG tracing is mechanical or physiologic. Thus, it would be an improvement in the art to have a system that makes such a differentiation. Accordingly, it is desirable to provide a method for detecting errors in wireless data transmissions relating to medical device communications, which is robust in the presence of various sources of interference or noise.

SUMMARY OF THE INVENTION

The present invention provides apparatus and method for detecting errors in a network communication channel that comprises a medical instrument such as a programmer that receives an ECG data stream from at least one IMD during a programming procedure. The networks to which the programmer is attached have sufficient throughput to transfer the ECG data stream to provide a high quality ECG tracing. There is, however, the potential for temporary interruptions of the data stream signals when these pass through network hubs, concentrators, and routers. Such interruptions may result in a loss of the ECG signal. Generally this loss of signal may last for only a fraction of a second. As such, the momentary loss of signal usually has a negligible impact on clinical and diagnostic practice when an experienced practitioner staffs the programmer. Nonetheless, an inexperienced clinician may be confused by the momentary pause in the ECG tracing.

The ECG data stream may be transferred via UDP (User Diagram Protocol) data packets with error detection codes, such as cyclic redundancy codes, imbedded within the data packets as is disclosed in U.S. Pat. No. 5,745,479 issued to Burns, et al., and incorporated herein by reference in its totality. The present invention, however, discloses an alternative error detection scheme that recognizes interruptions in the flow of UDP data packets. Processing software in the programmer is responsive to the interruption within the transmission of UDP data packets to detect errors.

The wireless communication channel in the programmer has a wireless link to a standard local area network. The UDP packets are transmitted from the IMD preferably using a radio frequency communication band, having a frequency on the order of 2 to 5 GHz. The UDP packets are transmitted from the IMD to the programmer, which includes software for identifying pauses in the received signal that are typical of erroneous data. The present invention provides client software that detects errors based on the interruption in the flow of UDP packets. When such an interruption occurs, the programmer's GUI software changes the color of the ECG tracing during the time of signal interruption.

The present invention will now be described with reference to the following drawings, in which like reference numbers denote the same element throughout.

DETAILED DESCRIPTION OF THE DRAWINGS

Figure 1:
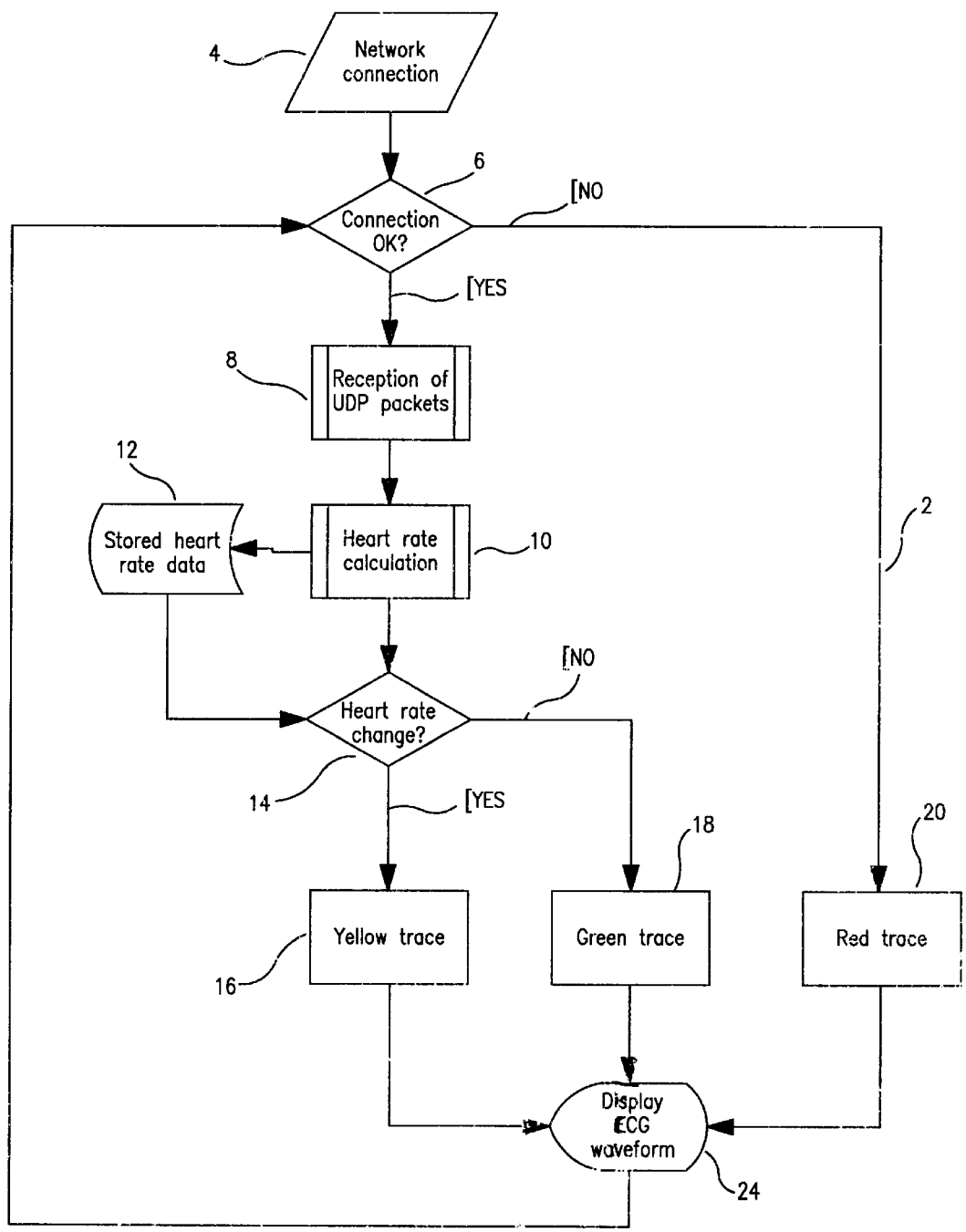
FIG. 1 is a flow chart illustrating the software logic in accordance with the present invention.

FIG. 1 is a flow chart illustrating the preferred embodiment of the present invention for color-coding of the ECG tracing by the programmer software. Software system 2 preferably resides in the programmer workstation (not shown) to continuously monitor network connection 4. Specifically, under decision step 6, the integrity of network connection 4 is checked to determine proper connection. If the connection is not made, the ECG tracing (see FIG. 2) will display a substantially straight colored line, for example, red trace 20 at ECG display 24. The colored line is used to indicate an interruption in the reception. Other colors that may more familiarly indicate interruptions in a given culture may be substituted. If there is no interruption in the signal at decision block 6, the software recognizes the uninterrupted reception of UDP packets 8 and begins heart rate calculation 10.

UDP is a communication method or protocol for communication that offers a limited amount of service when messages are exchanged between computers in a network that uses the Internet Protocol (IP). UDP is an alternative to the Transmission Control Protocol (TCP) and, together with IP, is sometimes referred to as UDP/IP. Like the TCP, UDP uses the IP to actually get a data unit (called datagram) from one computer to another. Unlike TCP, however, UDP does not provide the service of dividing a message into packets (datagrams) and reassembling it at the other end. Specifically, UDP doesn't provide sequencing of the packets that the data arrives in. This means that the application program that uses UDP must be able to make sure that the entire message has arrived and is in the right order or that the mis-ordering or loss of data is not of consequence. Network applications that want to save processing time because they have very small data units to exchange (and therefore very little message reassembling to do) may prefer UDP to TCP. The Trivial File Transfer Protocol (TFTP) uses UDP instead of TCP. UDP provides two services not provided by the IP layer. It provides port numbers to help distinguish different user requests and, optionally, a checksum capability to verify that the data arrived is intact.

Upon calculating heart rate 10, the software stores heart rate data 12 for continuous comparison to current heart rate for the purpose of detecting any change in heart rate 14. If there is no change in the heart rate, ECG tracing continues as color (green) trace 18 at ECG display 24. Although the color green is used in this embodiment to indicate continuity in the reception of UDP packets, other colors that may more familiarly indicate continuity in a given culture or technical discipline may be substituted. On the other hand, if there is a sudden and significant heart rate change noted at decision block 14, the ECG tracing will change to color (yellow) trace 16 for subsequent display 24. Sudden and significant change in heart rates under decision block 14 may be user defined. For example, a change in heart rate of 30 bpm, whether up or down, may be of clinical significance for one patient, whereas a rate of 15 bpm may be noteworthy in another patient. Again, color (yellow) trace 16 may be changed to a color judged more suitable to a given culture or user to indicate a significant change in heart rate.

Alternative embodiments may use more sophisticated algorithms to determine continuous or changed heart rates, e.g., waveform analysis via the correlation method. In this method, the ECG waveforms may be compared with the previously stored waveform template using cross correlation. If the waveforms do not correlate, ECG display 24 will change to yellow trace 16 to indicate a sudden change in rate. If the waveforms correlate with the template, ECG display at step 24 will be green trace 18.

Figure 2:
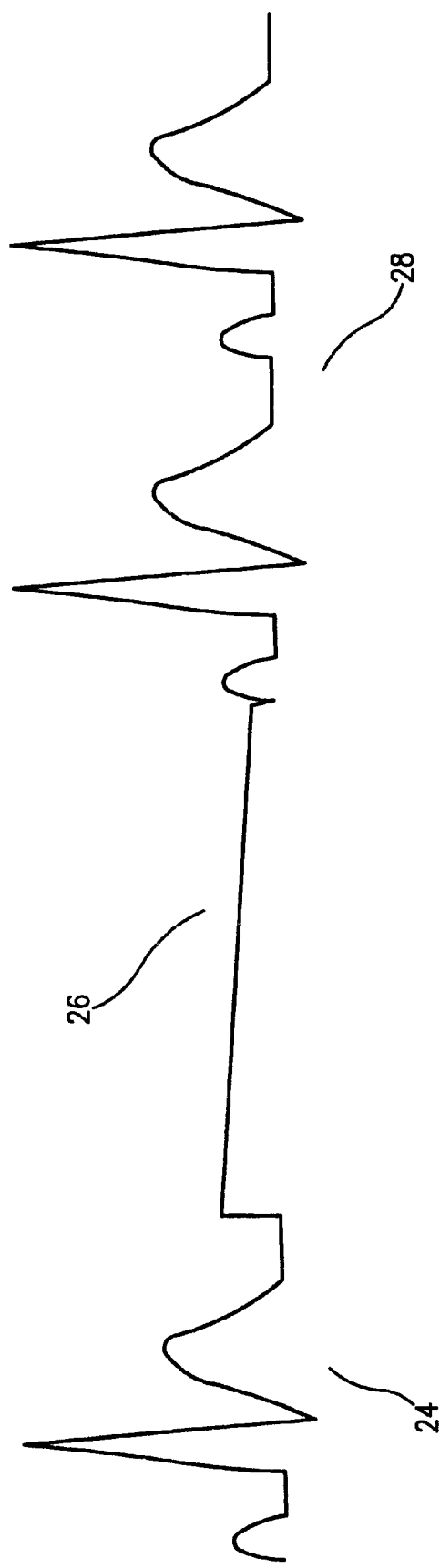
FIG. 2 is an illustration of an ECG tracing with a straight horizontal line (color coded) indicating an interruption in the reception of UDP packets.

FIG. 2 illustrates a process by which the software displays an ECG tracing when the transmission of UDP packets is interrupted. ECG waveforms 24 (QRST in this instance) will be displayed as color (green) trace until such time as an interruption in UDP packets occurs. Upon detection of such an interruption, horizontal straight line 26 (color-coded in red) is displayed on the programmer screen for about one second. Such an interruption in transmission may occur due to the switching of routers that typically occur in Internet transmission, for example.

Figure 3:
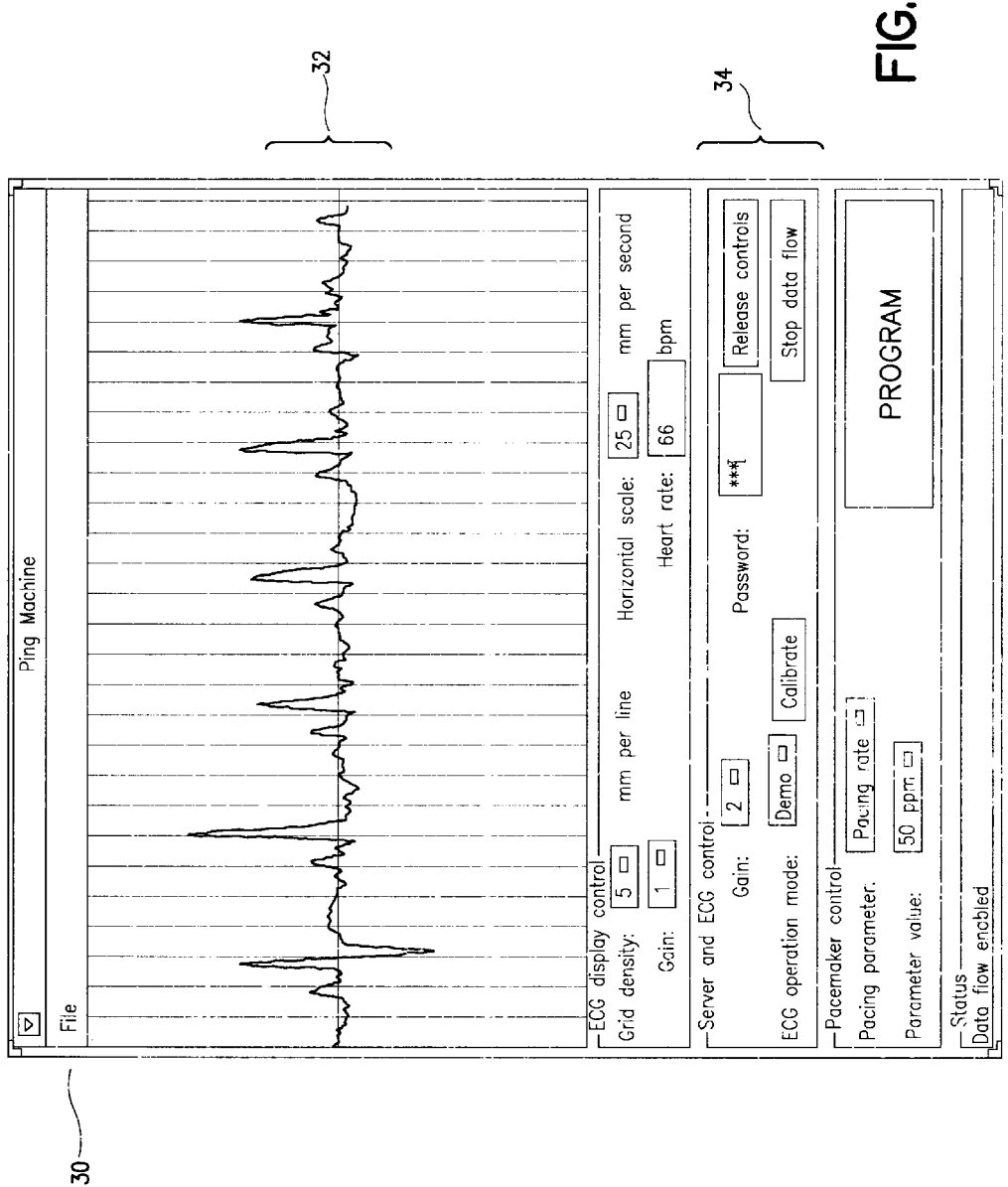
FIG. 3 is an illustration of how an ECG receiver, such as a programmer, processes and displays an uninterrupted ECG signal.

FIG. 3 illustrates another embodiment, wherein an ECG receiver such as a programmer receives a continuous, uninterrupted ECG data stream. ECG tracing 32 is displayed preferably as a white, or other light color, against a black or other dark color background when there is no interruption in the network connection(s) or in the transmission of the UDP packets. Thus, the ECG is preferably displayed as a negative trace against a positive background. ECG display controls 34 are similar to those found in a programmer and are well known to those who are familiar with the art. In this embodiment, the client software in the programmer is preferably connected to the Internet function as a virtual Java machine or equivalent In one aspect of the invention a computer platform and language adaptable for implementation is Java™ that may be provided by Sun Microsystems, Inc., San Jose, Calif. Java is a high-level, object-oriented interpreted programming language being architecture-neutral and portable. Java has a compiler for translating a Java program into an intermediate language called Java bytecodes, the platform-independent codes interpreted by the Java interpreter. With an interpreter, each Java bytecode instruction is parsed and run on the computer. Compilation happens just once; interpretation occurs each time the program is executed. Java bytecodes are like the machine code instructions for the Java Virtual Machine (Java VM). Every Java interpreter, whether it is a Java development tool or a Web browser that can run Java applets, is an implementation of Java VM. The Java VM can also be implemented in hardware. The Java platform has two components: the Java VM and the Java Application Programming Interface (Java API). The Java API is a large collection of ready-made software components that provide many useful capabilities, such as graphical user interface (GUI) widgets. The Java API is grouped into libraries (packages) of related components. Probably, the most well known Java programs are Java applets. An applet is a Java program that adheres to certain conventions that allow it to run within a Java-enabled browser. Common types of Java programs are also applications, where a Java application is a stand-alone program that runs directly on the Java platform. A special kind of application, known as a server, aids and supports clients on a network to recognize interruptions in data streams.

Figure 4:
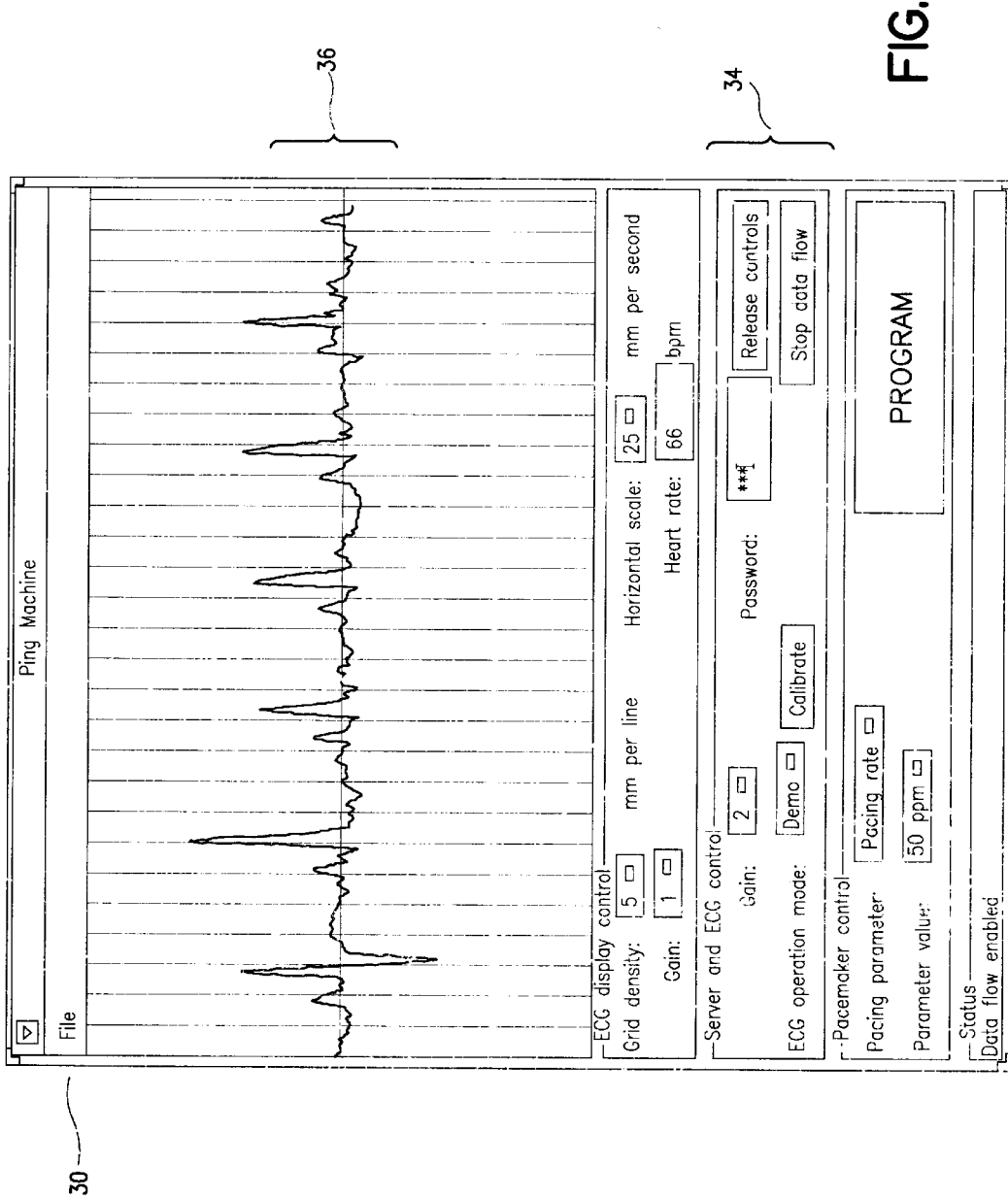
FIG. 4 is an alternative embodiment of how an ECG receiver, such as a programmer, processes and displays an interrupted ECG signal.

Further, other specialized programs are servlets that are similar to applets in that they are runtime extensions of applications. Instead of working in browsers, servlets run within Java servers, configuring or tailoring the server. A huge variety of implementations of this invention, which may be done using the Java platform and language, prohibit a precise disclosure of all the aspects. FIGS. 3 and 4 are only examples for purposes of illustration. Those skilled in the art may use Java in numerous possible modes because it is among the most dynamic, simple, and multithreaded computer platform and language.

FIG. 4 is a variation of FIG. 3 in which the ECG tracing 36 is displayed in a different manner. Specifically, ECG tracing 36 is shown as the obverse of that displayed in FIG. 3, that is, a positive, black or dark, tracing against a negative, white or light background. ECG display controls 34 are the same as those shown in FIG. 3. When ECG display 36 appears as a dark tracing against a light background, the user would immediately understand that an interruption in the transmission of the ECG data stream had occurred.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. A computer implemented software system to distinctively mark corruption, interruption and variations in a display of medical information obtained from a medical device via an instrument, the software system in combination with the medical device and the instrument comprising:

a network connection;

means for transferring data packets;

means for marking the data packets; and means for displaying the medical information;

said network connection providing data communication between the medical device and the instrument;

wherein said means for displaying is incorporated in the instrument to display said data packets;

wherein said means for marking represents the corruption, interruption and variations in said data packets;

wherein said medical device is an implanted medical device collecting the medical information in a patient.

2. The combination of claim 1 wherein said network connection is in operable data communication between the medical device and the instrument.

3. The combination of claim 1 wherein said instrument is one of a programmer, a home monitor and a personal computer (PC).

4. The combination of claim 1 wherein said data packets include user diagram protocol data packets.

5. The combination of claim 1 wherein said means for displaying includes a display screen.

6. The combination of claim 1 wherein said means for marking the data packets distinguishes between non-interrupted, unadulterated data packets and data packets that are suspect of interruptions and corruption.

7. The combination of claim 6 wherein said means for marking identifies interrupted or corrupt data packets by using line-size variations.

8. The combination of claim 7 wherein said means for marking identifies interrupted or corrupt data packets by using different colors.

9. The combination of claim 6 wherein the medical information is compared to stored data to determine the variations in medical condition of a patient.

10. The combination of claim 9 wherein the variations include one of a distinguishing color code and a marker.

11. The combination of claim 9 wherein non-variations between the medical information and said stored data include one of a distinguishing color code and a marker.

12. A method for distinguishing data interruption, corruption and variation in a display of a medical information obtained from a medical device via an instrument, the method comprising:

providing a network connection;

transmitting medical information from the medical device to the instrument via said network connection;

distinguishing the data interruption, corruption and variation; and displaying the data interruption, corruption and variation to alert a user about conditions of the data;

wherein the distinguishing aspect includes the use of markers;

wherein the use of markers includes line-size variations.

13. The method of claim 12 wherein the transmitting aspect includes the use of a wireless transmission system.

14. The method of claim 12 wherein the use of markers includes various colors.

15. A medical information system integrated with at least one implanted medical device (IMD) and an instrument to identify and display data corruption; variance, abnormalities and network connecting integrity, the system comprising:

a data network connecting the IMD with the instrument;

means for confirming the network connection;

means for transferring data packets from the IMD to the instrument;

means for comparing stored medical information with real-time medical information to detect the variance in a manner to identify data corruption and abnormalities; and means for identifying network connection problems and the variance;

a display means displays one of and combinations of distinctive colors and line markers to identify said network connection problems and the variance to enable a user to evaluate the IMD via said display means at the instrument.

16. The system of claim 15 wherein said means for confirming the network connection includes a logic set in the software that enables to display the medical information that is uninterrupted in a format that is distinguished from medical information obtained during a connection malfunction.

17. The system of claim 16 wherein said information obtained during said connection malfunction includes one of a color and a line trace distinguished from the medical information obtained during normal connection.

18. The system of claim 15 wherein said means for comparing includes identifying marks to distinguish between conforming and non-conforming data.

* * * * *